(12) United States Patent
Grottel et al.

(10) Patent No.: US 8,340,242 B2
(45) Date of Patent: Dec. 25, 2012

(54) DEVICE TO TRANSFER HIGH FREQUENCY ELECTRICAL SIGNALS BETWEEN A ROTATING COMPONENT AND A STATIONARY COMPONENT

(75) Inventors: Joachim Grottel, Lauf (DE); Andreas Troeltzsch, Heroldsbach (DE); Ludwig Welker, Eggolsheim (DE)

(73) Assignee: Siemens Aktiengesellschaft, Munich (DE)

( * ) Notice: Subject to any disclaimer, the term of this patent is extended or adjusted under 35 U.S.C. 154(b) by 399 days.

(21) Appl. No.: 12/784,004

(22) Filed: May 20, 2010

(65) Prior Publication Data

US 2010/0301680 A1  Dec. 2, 2010

(30) Foreign Application Priority Data

May 28, 2009  (DE) .......................... 10 2009 022 959

(51) Int. Cl.
*A61B 6/00* (2006.01)
(52) U.S. Cl. ......................................................... 378/15
(58) Field of Classification Search ................. 378/4–27
See application file for complete search history.

(56) References Cited

U.S. PATENT DOCUMENTS

| 3,811,743 | A | 5/1974 | Wren ............................. 384/475 |
| 6,356,002 | B1 | 3/2002 | Witherspoon et al. ......... 310/232 |
| 7,105,983 | B2 | 9/2006 | Day et al. ................ 310/323.01 |
| 7,339,302 | B2 | 3/2008 | Lewis et al. .................... 310/232 |

FOREIGN PATENT DOCUMENTS

DE  10 2005 003 203 B3  1/2006

*Primary Examiner* — Courtney Thomas
(74) *Attorney, Agent, or Firm* — Schiff Hardin LLP

(57) ABSTRACT

A device for the transfer of high frequency electrical signals between a rotating component and a stationary component, in particular for use in a CT system, in particular in a gantry of a CT system has a rotor, a stator; at least one brush attached at the stator, with a number of electrically conductive fibers that establish sliding contact with the rotor, and a slideway arranged to the side of the rotor and facing toward the stator. The fibers of the at least one stator-side brush rest on the slideway. A lubricant is provided on the slideway, a rotor has a capture device for the lubricant that is arranged around the outside of the slideway, and at least one return element for the captured lubricant is attached at the stator.

23 Claims, 3 Drawing Sheets

DEVICE TO TRANSFER HIGH FREQUENCY ELECTRICAL SIGNALS BETWEEN A ROTATING COMPONENT AND A STATIONARY COMPONENT

BACKGROUND OF THE INVENTION

1. Field of the Invention

The present invention concerns a device to transfer high frequency electrical signals between a rotating component and a stationary component, which includes a rotor; a stator; at least one brush with a number of electrically conductive fibers attached at the stator, the fibers establishing a sliding contact with the rotor; and a slideway arranged to the side of the rotor and facing toward the stator, on which the fibers of the at least one stator-side brush rest.

2. Description of the Prior Art

Devices that are used to transfer high frequency electrical signals are known, such as plate slip rings that essentially represent a rotating connection. In the following, the designation "slip ring" is also used for these types of connections. These slip rings are produced in various sizes; their diameters range from a few millimeters to nearly two meters for computed tomography. Slip rings can be used, for example, to transfer the digital image data and also to supply power to the x-ray source.

High frequency signals or currents can be transferred between a static component and a rotating component (thus between stator and rotor) with these rotating connections. In general, the stator together with one or more brushes (made from very thin, electrically conductive fibers, for example from silver) forms a sliding contact with the rotor, wherein the brush contacts touch the slideway of the rotor at their ends and thus establish the contact. For example, this is known from U.S. Pat. No. 7,105,983 B2.

In this patent, a slip ring to establish an electrical contact between a stator and a rotor is described, wherein the stator has a current-conducting conductor with a fiber bundle formed by individual fibers, the ends of which point toward the stator are fixed in a brush tube. The other end of the fiber bundle rests on the rotor and thus forms the sliding contact. Furthermore, a collimator tube is provided that surrounds the fiber bundle at its transition to the brush tube and thus should at least partially reinforce the fibers in order to prevent bending of the fibers that is too severe given a rotation of the rotor.

In the known slip rings it is problematic that the sliding contact cannot be maintained perfectly over a longer time span and at high rotation speeds of the rotor. The cause lies in the sliding movement of the brush fibers over the slideway since at least some of these temporarily stick to the slideway rather than sliding. If such slip rings are used in CT systems to acquire tomographic images, this means a data loss or an incorrect transfer of data sets can occur. In addition to the reduced quality of the data and current transfer, significant wear of the slideway and the brushes results from an incorrect sliding contact due to the mechanical movement between the components, and increased maintenance and cost expense result.

SUMMARY OF THE INVENTION

An object of the invention is to provide an additionally improved device with which high frequency electrical signals can be transferred without wear and error between a stationary component and a rotating component.

The invention is based on the insight that there is a positive influence on the quality and service life (thus also on the maintenance and cost expense) of a plate slip ring when a lubricant is introduced between the components that form the sliding contact for signal transfer. The mechanical movement between the slideway and the brushes is thereby ensured in a friction- and wear-free manner. The lubricated brush fibers can slide unhindered across the slideway without temporarily adhering to it (and thereby experiencing wear). In order to prevent the lubricant from being carried downward due to the centrifugal forces acting because of rotation, and in order to achieve a durable lubrication of the slideway, the lubricant can be held on the slideway and uniformly distributed on the slideway.

Under specific conditions, the lubricant can be held on the slideway by the capillary action of the brush fibers and by the adhesion forces acting between the lubricant and the slideway. As of a specific rotation speed, the force of the capillary action and the adhesion is smaller than that of the centrifugal force due to rotation. The lubricant is then drawn from the brush fibers, and it is first carried outward on the slideway and then thrown downward therefrom. Primarily in CT systems in which the rotation speed of the gantry (of less than one second per rotation) exceeds this limit value, enormous forces act on the lubricant. The result is an unlubricated slideway with a high wear both at the brush and on the track, and an unmonitored impedance change that has a disruptive effect (in particular on the transfer of high frequency signals) and can lead to a data loss.

Therefore the additionally improved slip ring can be equipped at least on the outside of the slideway with a capture device encompassing the entire circumference of the slideway. The lubricant flung outwardly by the centrifugal forces caused by rotation can be caught with this capture device. The inside of the slideway can also optionally be equipped with a capture device, such that the lubricant can likewise be captured on the entire circumference of the slideway during a standstill of the rotor—thus upon interruption of the centrifugal forces.

These capture devices should be produced from a non-absorbent, non-porous material so that the lubricant (for example an oil) continues to remain available at the capture devices.

In the lubrication of the slideway, care is to be taken that the lubricant is distributed uniformly. The disadvantages described above and known from the prior art, such as temporary adhesion of the brush fibers on the slideway, result due to too little lubricant. Too much applied lubricant, however, has a negative effect on the transfer quality and the service life of slideway and brushes. Over-lubrication—thus too much lubricant between the slideway and the brushes—can lead to arcing and damage to the components and to floating of the brushes, which leads to the loss of contact between the brushes and the slideway.

For this reason, in addition to a capture device, the additional improvement of the device should contain a return element for the lubricant, which transports the captured lubricant back to the slideway.

The captured lubricant can be transported back to the middle of the slideway by a return element attached at the stator that can be designed similar to the blade of a snow plow, such that it takes up the lubricant from the capture device from the edge of the slideway and transports it at least into the middle of the slideway.

Usage of quickly rotating plate slip rings with lubricated slideway for the undisrupted transfer of high frequency signals and energy transmission (in particular in CT systems)

over a long time period is possible for the first time with these additional improvements (capture device and returning element).

Such a device for the transfer of high frequency electrical signals between a rotating component and a stationary component is suitable for use in a CT system, in particular in a gantry of a CT system having a rotor; a stator; at least one brush attached at the stator, with a number of electrically conductive fibers that establish a sliding contact with the rotor; and a slideway arranged to the side of the rotor and facing toward the stator, on which slideway the fibers of the at least one stator-side brush rest. A lubricant is provided on the slideway; the rotor having a first capture device for the lubricant, which first capture device is arranged around the outside of the slideway; and at least one return element for the captured lubricant is attached at the stator.

In an embodiment of the invention, the first capture device (thus the one on the outside of the slideway) can exhibit a concave curvature in the direction of the centrifugal force. At the side facing toward the slideway, this curvature can be designed such that here at least the lubricant carried outwardly by centrifugal force can be captured.

In a further embodiment of the invention, a second capture device that extends around the entire inner side of the slideway is provided. The lubricant which would drop down from the slideway here upon a standstill of the rotor can then be captured with the second capture device. The second capture device can be designed to be at least partially concave, at least on its side facing toward the slideway; it can thus exhibit a curvature that is directed inwardly into the inside of the capture device. During a standstill of the rotor, only weight acts on the lubricant, and as soon as this is greater than the adhesion forces at the slideway the lubricant in the upper part of the slip ring drips downwardly (following the force of gravity) toward the middle point of the rotor and can be captured by the second capture device, such that it is available again upon a restart of the rotor. The roles of first and second capture device are interchanged in the lower part of the slip ring, and the lubricant dripping downwardly can be captured by the first capture device on the outside of the slideway.

The first capture device (and the second capture device, if present) preferably are formed of a material that does not absorb the captured lubricant in order to be able to provide it again for lubrication of the slideway. Furthermore, it is useful for the capture devices to be formed of an electrically insulating material so that these devices cannot have a disruptive effect on signal transmission. For example, plastics such as PVC are suitable as material for these devises.

In another embodiment of the plate slip ring according to the invention the at least one return element has at least one plow-like lip attached at the stator and resting at least in the curvature of the outward capture device. The operation of this plow-like lip corresponds to that of the blade of a snow plow. It can accordingly convey the lubricant from the curvature back to the slideway. For this purpose, it can be advantageous for this lip to be curved at least centrally in the rotation direction. The center point of the curvature is thus located in the middle of the slideway, and in this case the returning lubricant is transported to the middle of the slideway. In another variant of the curvature, the curvature is displaced in the direction of the inside of the slideway, meaning that the curvature is most strongly pronounced in the region of the inside of the slideway. With a lip molded in such a manner, the returning lubricant can be transported beyond the middle of the slideway, to the inside. This variant has the advantage that the brushes that are typically arranged in the middle of the slideway are better lubricated since the lubricant is effectively carried downwardly through them by centrifugal forces. If the lubricant is transported only to the middle, the brushes are consequently not lubricated as well since—depending on the distance between the brushes and the lip—a portion of the lubricant has already been carried outwardly again. For this reason it is preferable to arrange the brushes following the returning element in the rotation direction.

The at least one plow-like lip can be formed of a material that does not absorb the lubricant, for example a non-porous material, since otherwise the lubricant is held in the return element and is not transported back to the slideway.

In another preferred exemplary variant, the plate slip ring according to the invention has at least one storage medium for the lubricant, this at least one storage medium being attached at the stator and resting on the slideway of the rotor so that it is moved over the slideway to distribute the lubricant. For this purpose, the at least one storage medium can be formed of a material that absorbs the lubricant, such as felt. Furthermore, it is useful to attach a storage medium in front of one of the brushes in the rotation direction so that the slideway is optimally provided with lubricant directly before that brush.

In a further preferred embodiment variant, the at least one return element is simultaneously used as a storage medium. For this purpose, the at least one plow-like lip of the return element is formed of a material that absorbs the lubricant, for example felt. In this case the storage medium can release the absorbed lubricant onto the slideway and simultaneously distribute it uniformly on the slideway. Positioning in front of a brush is also useful in this embodiment.

A highly viscous liquid—advantageously an oil or a fat—can be used as the lubricant. Lubrication properties are better with high viscosity, and the lubricant is not as easily carried from the slideway by the centrifugal forces since the adhesion forces between the slideway and the lubricant are greater than for a less viscous lubricant.

According to the invention, the fibers of the at least one brush and the slideway can be formed of an electrically conductive material (for example gold, brass or copper) so that the transfer of electrical signals is facilitated. Additional advantages are achieved if the fiber material is softer than the slideway material. An improved sliding contact thus can be established between the brush and the slideway, and more cost-effective and more easily exchanged brushes wear more quickly than the slideway on the slip ring, which is significantly more expensive and complicated to service.

In a further embodiment of the plate slip ring according to the invention, the slip ring exhibits acute angle relative to the direction of the effective centrifugal force, which angle can be adjusted depending on the rotation speed with which the slip ring is typically operated. The outside of the slideway is preferably more sharply angled compared to the inside of the slideway. The lubricant is then prevented from being carried out of the slideway by an additional force component perpendicular to the rotation plane, before it can be captured by the first capture device.

Furthermore, the invention encompassed a gantry (in particular for use in a CT system) that embodies a device according to the invention for the transfer of high frequency electrical signals.

In the following the invention is described in detail using the preferred examples with the use of the figures, wherein it is noted that only the elements that are essential for the immediate understanding of the invention are shown. The following reference characters are hereby used: 1: rotor; 2: slideway; 3: first capture device; 4: second capture device; 5: lubricant; 6: curvature of the first capture device; 7: curvature of the second capture device; 8: brush; 9: lip; $Z_F$: centrifugal force; C1: CT system; C2: first x-ray tube; C3: first detector; C4: second x-ray tube (optional); C5: second detector (optional); C6: gantry housing; C7: patient; C8: displaceable patient bed; C9: system axis; C10: control and computation unit; $Prg_1$ through $Prg_n$: computer program or program module; $\vec{v}$: rotation speed.

DESCRIPTION OF THE PREFERRED EMBODIMENTS

Figure 1:
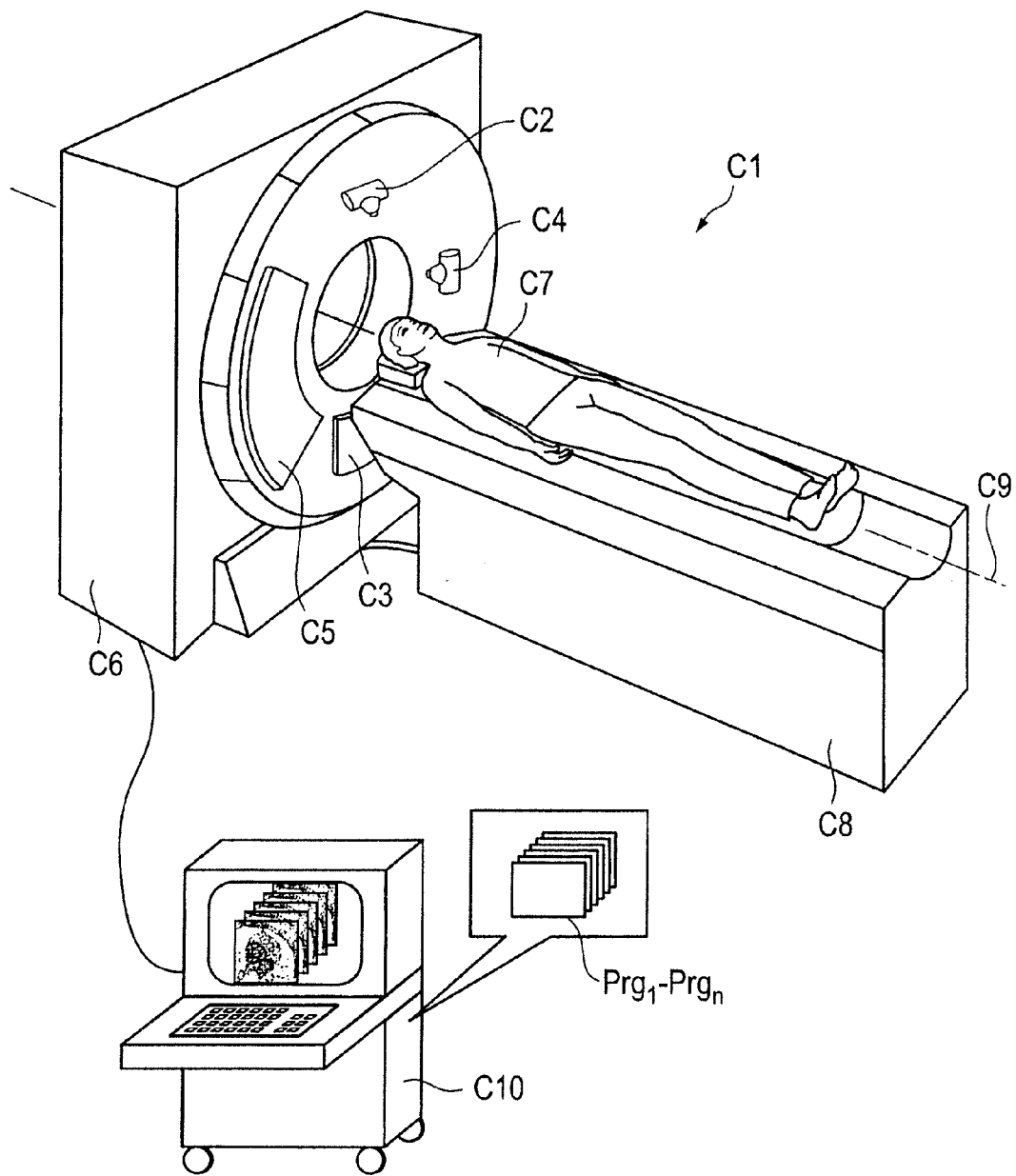
FIG. 1 schematically shows a CT system.

Shown by way of example in FIG. 1 is a computed tomography (CT) system C1 with a detector C3. This CT system C1 has a gantry housing C6 in which a gantry is located with an x-ray tube C2 that, together with a detector C3 situated opposite the x-ray tube C2, rotates around a system axis C9. At least one second x-ray tube C4 and a detector C5 situated opposite it can optionally be arranged on the gantry. Depending on the scanning, the sampling rate can hereby be increased, or another scan (for example a phase contrast scan) can be achieved. For scanning a patient C7 (for example) on a patient bed C8 is slid through the measurement field while the x-ray tubes C2 and C4 and the detectors C3 and C5 on the gantry rotate around the system axis C9.

The gantry contains a plate slip ring according to the invention for the transfer of the measured signals and to supply power to the x-ray sources, with a stator and a rotor that rotates around the system axis C9.

The signals detected by the detector C3 can be processed directly with an electronic detector unit in a central control and computation unit C10. Computer programs $Prg_1$-$Prg_n$ can also be stored there.

Figure 2:
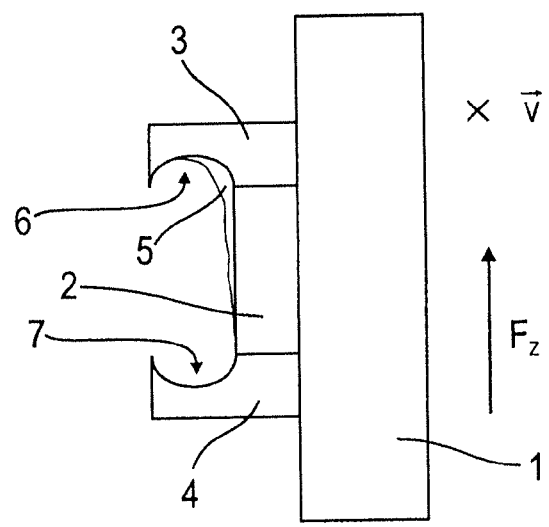
FIG. 2 is a cross-section through a slideway with capture devices in accordance with the invention.

FIG. 2 shows a cross section through a slideway 2 attached at the side on the rotor 1. In this depiction a cross section through the slideway 2 was selected in the upper region of the rotor 1. The capture devices 3 and 4 are located around the slideway 2 on both sides. A lubricant 5 is apparent on the slideway 2 itself. A centrifugal force $F_z$ occurs due to the rotation of the rotor 1, wherein the rotation direction is shown with the rotation speed $\vec{v}$ into the plane of the drawing and is marked by an x. As soon as the centrifugal force $F_z$ caused by the rotation is greater than the adhesion forces that hold the lubricant 5 on the slideway 2 up to a specific rotation speed $\vec{v}$, the lubricant 5 is carried outwardly in the direction of the acting centrifugal force $F_z$. In this depiction (selected as an example) the outside of the slideway 2 is located in the upper area of the image. The lubricant 5 carried outwardly can be captured in the first capture device 3 on the outside of the slideway 2. For this the capture device 3 is partially molded in a concave shape, thus with a inwardly directed curvature.

The second capture device 4 arranged on the inside of the slideway 2, which capture device 4 is likewise shaped partially concave on its side facing towards the slideway so that a curvature 7 is created, can capture lubricant 5 dripping downward when the rotor 1 is at a standstill. In this case centrifugal force $F_z$ no longer acts on the lubricant 5, rather only gravity that draws the lubricant 5 downward. In the lower portion of the rotor 1 (not shown here), the first capture device 3 accordingly catches lubricant 5 dripping downwardly.

In the lower region of the rotor 1 (not shown) with the slideway, the roles of the first and second capture device 3 and 4 are thus interchanged. The first capture device 3 on the outside of the slideway catches lubricant 5 dripping downward and the second capture device catches lubricant 5 carried outward. The transition from the lower region to the upper region is thereby fluid, dependent on rotation.

Figure 3:
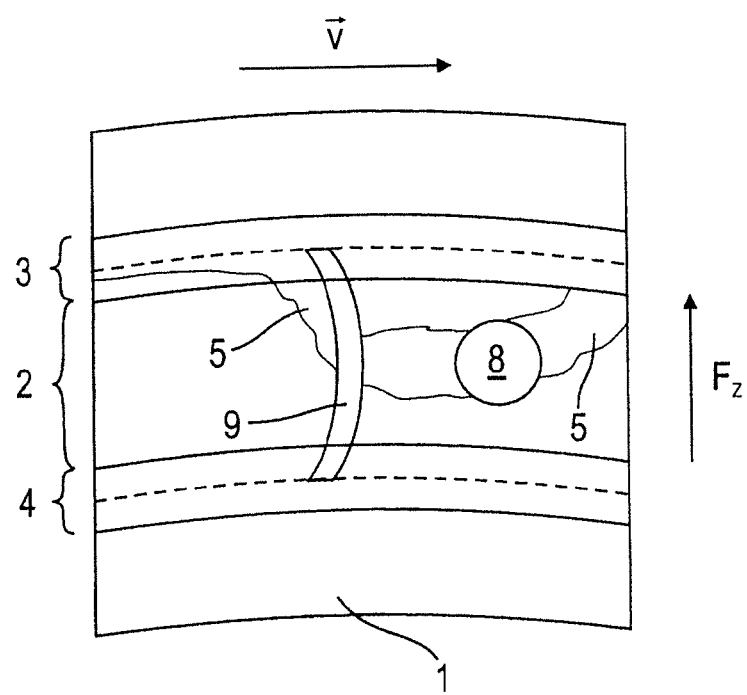
FIG. 3 is a plan view of a slideway with capture devices, lip and brush in accordance with the invention.

FIG. 3 shows the plan view of a section of a rotor 1 with a slideway 2 arranged thereupon according to FIG. 2. The direction of the rotation velocity $\vec{v}$ of the rotor is marked with an arrow. A brush 8 attached at the stator is located on the slideway 2. Its brush fibers that rest on the slideway 2 and establish the sliding contact between stator and rotor are not recognizable in this depiction. For a better overview, the attachment of the brush 8 on the stator and the stator itself are not shown. A return element in the form of a plow-like lip 9 is likewise attached at the stator, between the capture devices 3 and 4 arranged around the slideway, which lip 9 rests on the slideway 2 and in the curvatures of the capture devices 3 and 4. The lip 9 has a curvature in the direction of the rotation direction.

The slideway 2 moves relative to the stationary lip 9 due to the movement of the rotor 1. The curvature of the lip 9 thereby collects the lubricant 5 from the capture device 3 and transports it back into the middle of the slideway 2, where it is again available for lubrication. In this exemplary embodiment of the slip ring, the brush 8 is located directly after the returning element in the rotation direction, such that the slideway is optimally lubricated immediately in front of the brush 8. Due to the centrifugal force $F_z$ continuously acting during the rotation of the rotor 1, as soon as it has been brought back to the slideway 2 by the lip 9 the lubricant 5 is carried outward again, where it is caught by the capture device 3. Therefore it is reasonable to not select the distance between lip 9 and brush 8 to be too large.

In one embodiment, the plow-like lip according to the invention can be produced from a material that absorbs the lubricant 5 (for example felt) and thus it can simultaneously serve as a storage medium for the lubricant 5. A felt can absorb the lubricant 5 and subsequently lubricate the slideway 2 continuously and uniformly as the lubricant is carried away, similar to a paint brush.

Figure 4:
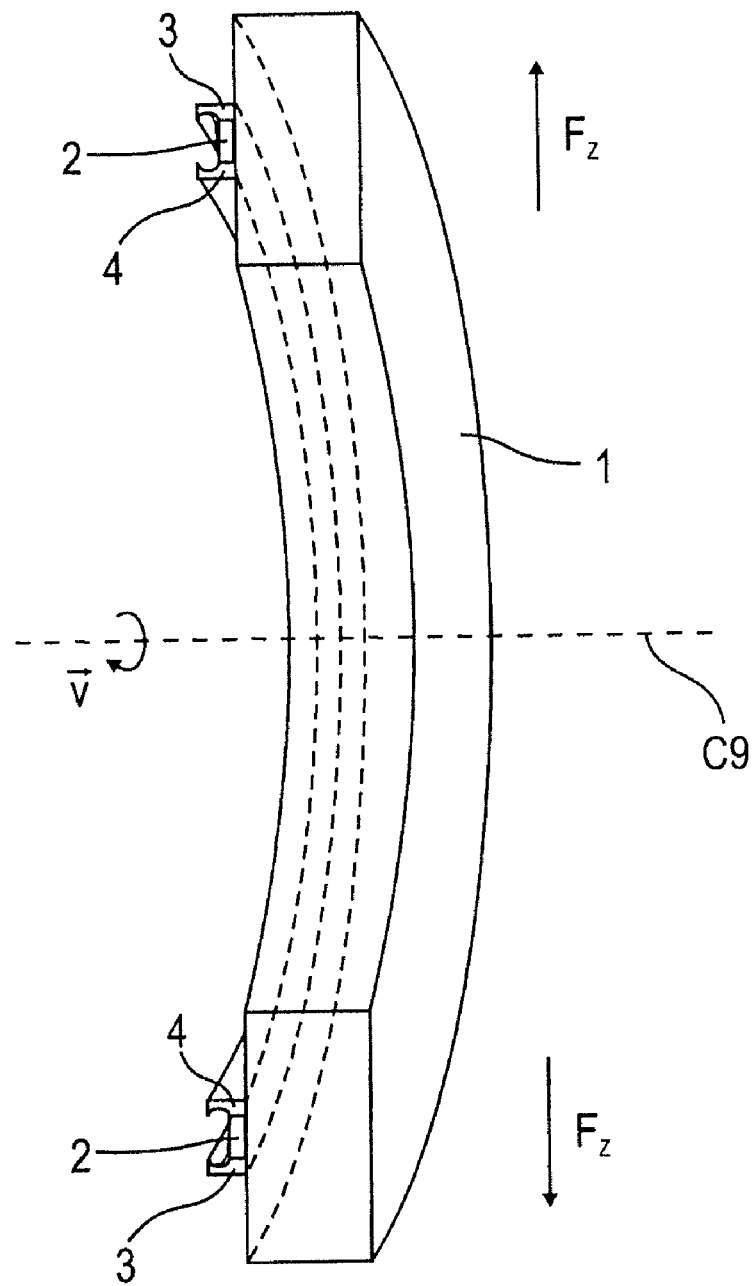
FIG. 4 is a cross-section through a rotor with slideway and capture devices in accordance with the invention.

FIG. 4 shows a radial cross section through a rotor 1 of a plate slip ring with slideway 2 mounted at the side. According to FIGS. 2 and 3, the capture devices 3 and 4 are arranged around the slideway. The rotor 1 rotates around the system axis C9 with a rotation velocity $\vec{v}$, wherein the outwardly directed centrifugal force $F_z$ carries the lubricant 5 applied on the slideway 2 outwardly. The lubricant 5 can be caught by means of the capture device 3 and be transported back to the slideway 2 via the returning element (not shown here).

Although modifications and changes may be suggested by those skilled in the art, it is the intention of the inventors to embody within the patent warranted hereon all changes and modifications as reasonably and properly come within the scope of his or her contribution to the art.

We claim as our invention:
1. A device for transferring high frequency electrical signals between a rotating component and a stationary component, comprising:
a stator;
a rotor that rotates relative to said stator;

at least one brush attached to said stator, comprising a plurality of electrically conductive fibers that establish a sliding electrical contact with the rotor;

a slideway mounted at a side of the rotor facing toward the stator, said brush being attached to said stator with the fibers thereof resting on the slideway;

a lubricant located in the slideway;

a capture device at the rotor configured to capture lubricant at a location in the slideway to which the lubricant is moved by centrifugal force occurring upon rotation of said stator; and at least one return element in fluid communication with said capture device that returns lubricant captured by the capture device to the slideway, said return element being attached at the stator.

2. A device as claimed in claim 1 wherein said capture device has a side facing toward the slideway that is at least partially concave in shape.

3. A device as claimed in claim 1 wherein said capture device is a first capture device, and comprising a second capture device, that also captures lubricant in the slideway, located around an inner side of the slideway.

4. A device as claimed in claim 3 wherein said second capture device has a side facing toward the slideway that is at least partially concave in shape.

5. A device as claimed in claim 3 wherein said first and second capture devices are comprised of a material that does not absorb the captured lubricant.

6. A device as claimed in claim 3 wherein the first and second capture devices are comprised of an electrically insulating material.

7. A device as claimed in claim 1 wherein said at least one return element comprises a plow-like lip attached at the stator and resting against said capture device.

8. A device as claimed in claim 7 wherein said plow-like lip is curved at least centrally in a direction of rotation of the stator.

9. A device as claimed in claim 7 wherein said plow-like lip comprises a curvature in a direction of rotation of the stator, said curvature being most strongly pronounced in a region at an interior of the slideway.

10. A device as claimed in claim 7 wherein said plow-like lip is comprised of a material that does not absorb the lubricant.

11. A device as claimed in claim 1 comprising a storage medium for the lubricant.

12. A device as claimed in claim 11 wherein said storage medium is attached at the stator and rests on the slideway of the rotor.

13. A device as claimed in claim 11 wherein said storage medium is attached at the stator at a location preceding said brush in a direction of rotation of the stator.

14. A device as claimed in claim 11 wherein said storage medium comprises a material that absorbs the lubricant.

15. A device as claimed in claim 11 wherein said return element simultaneously forms said storage medium.

16. A device as claimed in claim 15 wherein said return element comprises a plow-like lip comprised of a material that absorbs the lubricant.

17. A device as claimed in claim 1 wherein said lubricant is an oil.

18. A device as claimed in claim 1 wherein said lubricant is a fat.

19. A device as claimed in claim 1 wherein said fibers of said brush, and said slideway, are formed of a material selected from the group consisting of gold, brass and copper.

20. A device as claimed in claim 1 wherein said fibers of said brush are comprised of a material that is softer than a material that comprises said slideway.

21. A device as claimed in claim 1 wherein said slideway has a non-90° angle relative to a direction of centrifugal force acting thereon, dependent on said rotation speed.

22. A computed tomography gantry comprising:

a gantry frame comprising a stator mounted therein;

a rotor mounted in said gantry frame for rotation relative to said stator, said rotor being configured to co-rotatably carry computed tomography imaging components thereon;

at least one brush attached to said stator, comprising a plurality of electrically conductive fibers that establish a sliding electrical contact with the rotor;

a slideway mounted at a side of the rotor facing toward the stator, said brush being attached to said stator with the fibers thereof resting on the slideway;

a lubricant located in the slideway;

a capture device at the rotor configured to capture lubricant at a location in the slideway to which the lubricant is moved by centrifugal force occurring upon rotation of said stator; and at least one return element in fluid communication with said capture device that returns lubricant captured by the capture device to the slideway, said return element being attached at the stator.

23. A computed tomography apparatus comprising:

a gantry frame comprising a stator mounted therein;

a rotor mounted in said gantry frame for rotation relative to said stator;

an x-ray source and a radiation detector mounted on said rotor for co-rotation therewith to generate computed tomography data from an examination subject around which said rotor rotates;

at least one brush attached to said stator, comprising a plurality of electrically conductive fibers that establish a sliding electrical contact with the rotor;

a slideway mounted at a side of the rotor facing toward the stator, said brush being attached to said stator with the fibers thereof resting on the slideway;

a lubricant located in the slideway;

a capture device at the rotor configured to capture lubricant at a location in the slideway to which the lubricant is moved by centrifugal force occurring upon rotation of said stator; and at least one return element in fluid communication with said capture device that returns lubricant captured by the capture device to the slideway, said return element being attached at the stator.

* * * * *